United States Patent [19]

Miyake et al.

[11] Patent Number: 4,518,581
[45] Date of Patent: May 21, 1985

[54] IMPARTING LOW- OR ANTI-CARIOGENIC PROPERTY TO ORALLY-USABLE PRODUCTS

[75] Inventors: Toshio Miyake; Mikihiko Yoshida; Kanō Takeuchi, all of Okayama, Japan

[73] Assignee: Kabushiki Kaisha Hayashibara Seibutsu Kagaku Kenkyujo, Okayama, Japan

[21] Appl. No.: 428,117

[22] Filed: Sep. 28, 1982

[30] Foreign Application Priority Data

Nov. 2, 1981 [JP] Japan ............................... 56-174455
Dec. 28, 1981 [JP] Japan ............................... 56-210161

[51] Int. Cl.$^3$ .......................... A23G 3/00; A23G 3/30
[52] U.S. Cl. ...................................... 424/48; 424/49; 424/56; 424/57; 424/64; 426/3; 426/658; 426/660; 426/590; 131/274; 435/96; 435/99; 536/1.1
[58] Field of Search ................ 426/658, 3, 590, 660; 435/96, 99; 536/1.1; 424/48, 49, 180, 56, 57, 64; 131/274

[56] References Cited

U.S. PATENT DOCUMENTS

| 2,822,303 | 2/1958 | Campbell et al. | 426/658 X |
| 2,891,869 | 6/1959 | Langlois | 435/96 X |
| 3,249,512 | 5/1966 | Bode | 435/96 |
| 3,654,082 | 4/1972 | Abdullah | 435/99 X |
| 3,705,039 | 12/1972 | Mitsuhashi et al. | 536/1.1 X |
| 4,113,509 | 9/1978 | Leach et al. | 435/96 X |
| 4,281,028 | 7/1981 | Walon | 426/658 |
| 4,335,208 | 6/1982 | Norman | 435/96 |
| 4,346,116 | 8/1982 | Verwaerde | 426/658 |
| 4,357,314 | 11/1982 | Lynch | 424/49 |
| 4,381,318 | 4/1983 | Lynch | 426/658 |

FOREIGN PATENT DOCUMENTS

| 0753320 | 1/1971 | Belgium | 426/658 |
| 147801 | 11/1981 | Japan | 435/99 |
| 1181174 | 2/1970 | United Kingdom | 435/96 |
| 2049698 | 12/1980 | United Kingdom | 435/96 |

OTHER PUBLICATIONS

Allen, W. G. et al., "Technology and Uses of Debranching Enzymes", *Food Technology*, pp. 70–80, (May 1975).

Primary Examiner—Joseph Golian
Attorney, Agent, or Firm—Browdy and Neimark

[57] ABSTRACT

An invention providing a process for producing orally-usable products possessing low- or anti-cariogenic properties is disclosed. The process comprises preparing said products with, or adding thereto a saccharide having a substantial anti-cariogenicity. The saccharides preferred in the invention are isomaltosyl mono-, di-, tri-glucoses, and reduction products thereof; for example, panose, isomaltotriose, isomaltosyl maltose, isomaltotetraose, isomaltopentaose, and reduction products thereof, i.e., pannitol, isomaltotriitol, isomaltosyl maltitol, isomaltotetraitol, and isomaltopentaitol. Such saccharides can be used in the production of any products used orally, including foods and drinks in general, to impart thereto a substantial low- or anti-cariogenic property, as well as to sweeten them.

25 Claims, No Drawings

IMPARTING LOW- OR ANTI-CARIOGENIC PROPERTY TO ORALLY-USABLE PRODUCTS

BACKGROUND OF THE INVENTION

The present invention relates to a process for producing orally-usable products. More particularly, it relates to a process for producing orally-usable products including foods and drinks in generaly, feeds, pet foods, cosmetics, dentifrice, medicine and tobacco, having a substantial low- or anti-cariogenic property. Additionally, sweetness and an improved taste quality, is imparted to the products.

DESCRIPTION OF THE PRIOR ART

Large amounts of sucrose, a typical sweetener with sufficient sweetness and body, are used in the production of food products.

Recently, it has been established that sweetened food products, particularly, those sweetened with sucrose, very often cause dental caries. Dental caries are generally caused when the sucrose constituent in the food products is converted by oral cariogenic microorganisms into a water-insoluble glucin, e.g., dextran, which adheres in layers and reaches the tooth surface where it is fermented anaerobically into organic acids which eventually attack the tooth enamel.

Accordingly, the establishedment of a process for producing food products, using a natural sweetener with the lowest possible cariogenicity in place of sucrose, has been desired for years.

Although some processes for producing orally-usable products using sucrose coupled starch sugar (Coupling Sugar ®) or aldosylfructoside have been established hitherto, they do not completely satisfy the objectives of anticariogenicity. The use of such saccharides realizes a low-cariogenic sweetener, but does not provide anti-cariogenic food products directed to prevent dental caries.

SUMMARY OF THE INVENTION

It is one object of the present invention to provide a process for producing orally-usable products including food products in general which possess substantial low-cariogenic properties.

Another object of the invention is to provide a method for imparting substantial anti-cariogenic properties to orally usable products.

A further object of the invention is to provide a method for improving the taste and sweetness of orally-usable products for human- or non-human consumption.

These and other objects have been attained by a process which comprises preparing orally usable products with, or adding thereto one or more members selected from the group consisting of glycosyl mono-, di-, tri-glucoses, and reduction products thereof having anti-cariogenicity surpassing those of conventional low-cariogenic sweeteners.

DETAILED DESCRIPTION OF PREFERRED EMBODIMENTS

The present invention is based on the finding that isomaltosyl mono-, di-, tri-glucoses and reduction products thereof have substantial low- or anti-caroigenicities, as well as desirable sweetness, which renders the saccharides useful for producing orally-usable products possessing substantial low- or anti-cariogenic properties.

The isomaltosyl mono-, di-, tri-glucoses, and reduction products thereof usable in the invention are triose, tetraose and pentaose, consisting of either glucosyl units, or glucosyl and glucitol units, which bear isomaltosyl residues on their molecular ends. For example, one or more members of panose (4-O-α-isomaltosyl glucose), isomaltotriose (6-O-α-isomaltosyl maltose ($4^2$-O-α-isomaltosyl maltose), isomaltotetraose ($6^2$-O-α-isomaltosyl isomaltose), isomaltopentaose ($6^3$-O-α-isomaltosyl isomaltotriose), pannitol (4-O-α-isomaltosyl glucitol), isomaltotritol (6-O-α-isomaltosyl glucitol), isomaltosyl maltitol ($4^2$-O-α--isomaltosyl maltitol), isomaltotetraitol ($6^2$-O-α-isomaltosyl isomaltitol), and isomaltopentaitol ($6^3$-O-α-isomaltosyl isomaltotriitol) are favorably usable in the invention regardless of how they are produced. For example, panose and isomaltosyl maltose may be found in substantial amount in a partial pullulan hydrolysate obtained with the use of either acid or enzyme; and isomaltotriose, isomaltotetraose and isomaltopentaose may be found in a partial dextran hydrolysate obtained with the use of either acid or enzyme, a reversible-reaction product of glucose obtained with the use of either glucoamylase (EC 3.2.1.3) or acid catalyst, or in a glucose-transferred product of maltodextrin obtained with the use of α-glucosyl transferase or transglucosidase (EC 3.2.1.20).

Any of the isomaltosyl mono-, di-, and tri-glucoses may be reduced according to any conventional reduction method. For example, a 40–60% aqueous solution of the saccharide(s) is placed in an autoclave with 8–10% Raney nickel catalyst. While stirring, the mixture is heated therein to 90°–140° C. and catalytically hydrogenated at this temperature under a hydrogen pressure of 20–150 kg/cm$^2$. After completion of the catalytic hydrogenation, the catalyst is removed from the reaction mixture, and the residue is decolorized with activated carbon and deionized with the use of ion exchange resins, followed by concentration of the purified product to obtain a syrup. The syrup may be eventually dried and pulverized to obtain a powder.

Prior to use, the above described saccharide preparations may be purified. For example, fractionation, using an activated carbon column, an ion exchange resin column or gen filtration, or separation, using a glucose-removing membrane filter, may be employed to obtain a highly purified isomaltosyl mono-, di-, tri-glucose, or a reduction product thereof.

The isomaltosyl mono-, di-, tri-glucoses, and reduction products thereof are practically non-crystalline saccharides with desirable sweetness. They are only insifnificantly fermented by oral cariogenic microorganisms into either water-insoluble glucan or organic acid. Further, they inhibit the formation of water-insoluble glucan from sucrose. These properties suggest that they can be favorably used as low- or anti-cariogenic sweeteners.

Furthermore, in addition to sweetening, the saccharides can be advantageously used to impart appropriate viscosity, moisture, gloss or body to the orally-usable products, and/or to prevent crystallization of their crystalline constituents.

Although the sweetener according to the present invention may be used intact as a seasoning to sweeten products, a combined use with one or more sweeteners, e.g., sucrose, corn syrup, glucose, maltose, isomerized sugar, honey, maple sugar, sorbitol, maltitol, lactitol, dihydrocharcone, L-asparatyl phenylalanine methyl ester, saccharin, glycine, alanine, glycyrrhizin, stevioside, α-glycosyl stevioside, is desirable of its relatively low sweetening power.

Also, the sweetener can be used, if necessary, together with a filler, e.g., dextrin, starch, or lactose; a favoring agent; or a coloring agent.

Unlike sucrose, the substantial anti-cariogenicity of the sweetener does permit its use as a main- or submaterial for producing various food products for preventing dental caries.

The taste of the sweetener harmonizes well with the sour-, salty-, bitter-, astringent- or delicious-tasting substances used in food products in general to improve their taste qualities. For example, in seasonings, such as soy sauce, soy sauce powder, soy paste, soy paste powder, maonnaise, dressings, vinegar, powder vinegar, extracts fior Chinese-style foods, sauce, catsup, curry roux, extracts for stew and soup, mixed seasoning, and table syrup; confectioneries and bakery products, such as bread, biscuits, crackers, cookies, pies, jelly, castella, pudding, butter cream, custard cream, choux cream, waffles sponge cake, doughnuts, chocolate, chewing gum, toffee, rice paste, and candy; frozen-desserts, such as ice-cream and sherbet; syrups; pastes, such as flour paste, peanut paste and fruit paste; preserved foods, such as jam and marmalade; pickles and pickled products, such as pickled fruits and vegetables; meat products, such as ham and sausae; fish-meat products, such as fish-meat ham, and fish-meat sausage; daily dishes, such as potato salad; bottled and canned foods, such as canned meats, fruits and vegetables; soft drinks, such as coffee, cocoa, juice, carbonates drinks, sour milk beverage and yogurt drinks; and convenience foods, such as pudding, hot cakes, juice and coffee.

In addition to the above described general uses, the sweetener can be favorably used to improve the taste qualities of feeds and pet foods for domestic animals, honey bees, silkworms or fishes, as well as to improve the taste qualities of tobacco, dentifrice, lipstick, lipcream, drugs for internal administration, trouche, drops containing liver oil, cachou, oral refreshing agents or gargles, regardless of their final forms, i.e., liquid, paste or solid.

From the above descriptions, the term "orally-usable products", as used in the specification, shall mean all products which can be orally used, e.g., foods and drinks in general, tobacco, feeds, pet foods, cosmetics, and drugs, in conjunction with the sweetener according to the present invention.

As to the method to prepare the products with, or add thereto the saccharide, any method can be employed in the invention so far as the objective can be attained therewith; for example, kneading, mixing, dissolving, soaking, coating, applying or injecting.

Althoug the contents of the saccharide in the products may be freely chosen so far as the occurrence of dental caries is substantially inhibited therewith, if the saccharide is incorporated in the products together with sucrose, the content required for substantial inhibition is 5% or higher, preferably, 10% or higher.

The following experiments explain the present invention in further detail.

EXPERIMENT 1

Preparation of water-insoluble glucan producing enzyme solution

A seed culture of Streptococcus mutans 6715 strain was inoculated in a liquid medium, comprising 3.5% aqueous solution of Brain Heart Infusion Broth, purchased from Nissui Seiyaku Co., Ltd., Komagome, Toshima-ku, Tokyo, Japan, and cultured therein at 37° C. for 18 hours. After completion of the cultivation, the culture was separated into cell precipitant and supernatant. Thereafter, to the supernatant was added with ammonium sulfate to give 60% saturation, and the resultant precipitant was dialyzed against 0.1M phosphate buffer (pH 7.2) to obtain an aqueous solution containing the enzyme.

The titers of the enzyme were assayed as follows: A mixture solution, consisting of 1 ml of 0.2M aqueous sucrose solution, 1 ml of water, 1 ml of 0.1M phosphate buffer containing 0.05 w/v % $NaN_3$, and 0.5 ml of the enzyme solution (below 0.05 units), is incubated at 37° C. for 9 hours, followed by centrifugation of the reaction mixture. The resultant precipitant is mixed with 4 ml of 0.5N sodium hydroxide solution, and then incubated at this temperature for an additional one hour to dissolve the precipitant. The amount of water-insoluble glucan formed during the enzymatic reaction is then measured. One unit of the enzyme is defined as the amount of enzyme that transfers 1 μmole glucose from sucrose to the water-insoluble glucan in one minute.

EXPERIMENT 2

Formation of water-soluble glucan from some saccharides

The water-soluble glucan from some saccharides was tested: An experiment, wherein the sucrose constituent in the mixture solution for the enzyme assay was replaced with each of the saccharides listed in TABLE I, conformed that no significant water-insoluble glucan formation occurs.

EXPERIMENT 3

Effect of some saccharides on formation of water-insoluble glucan from sucrose

Effects of some saccharides on the formation of water-insoluble glucan were tested: Water-insoluble glucan formation and inhibition thereof were determined according to the enzyme assay method as described in EXPERIMENT 1, except that the mixture solution contained sucrose, or sucrose and each saccharide as listed in TABLE I. The experiment was carried out as follows: A mixture solution, consisting of 1 ml of 4 w/v % aqueous sucrose solution, 1 ml of 4 w/v % aqueous solution of each saccharide as listed in TABLE I, 1.5 ml of 0.1M phosphate buffer containing 0.05 w/v % $NaN_3$, and 0.5 ml of the enzyme solution (0.02 units), was incubated at 37° C. for 16 hours, and the water-insoluble glucan formation in the reaction mixture was determined according to the enzyme assy method.

In a control experiment, 1 ml of the above described saccharide solution was replaced with the same amount of water.

The results are given in Columns A and B in TABLE I, wherein Column A and B list the amounts of water-insoluble glucan formed (μg/ml) and inhibition degree on water-insoluble glucan formation (%). The inhibition degree was calculated with following equation:

Inhibition degree (%) = 100 − A/B × 100 where A and B are respective amounts of the water-insoluble glucan formed (μg/ml) when the mixture solution contained sucrose or sucrose and each of the saccharides.

TABLE I

| Saccharide | A (μg/ml) | B (%) | C (%) |
|---|---|---|---|
| Sucrose (control) | 300 | | |
| Sucrose plus L-Arabinose | 294 | 2 | — |
| Sucrose plus L-Sorbose | 261 | 13 | — |
| Sucrose plus Rhamnose | 300 | 0 | — |
| Sucrose plus D-Galactose | 297 | 1 | — |
| Sucrose plus D-Mannose | 294 | 2 | — |
| Sucrose plus D-Glucose | 285 | 5 | — |
| Sucrose plus Methyl-α-D-Glucose | 258 | 14 | — |
| Sucrose plus 2-Deoxy Glucose | 285 | 5 | — |
| Sucrose plus N—Acetyl glucosamine | 285 | 5 | — |
| Sucrose plus Turanose | 273 | 9 | — |
| Sucrose plus Lactulose | 264 | 12 | — |
| Sucrose plus Gentiobiose | 300 | 0 | — |
| Sucrose plus Cellobiose | 200 | 0 | — |
| Sucrose plus Melibiose | 300 | 0 | — |
| Sucrose plus Trehalose | 297 | 1 | — |
| Sucrose plus Maltulose | 180 | 40 | — |
| Sucrose plus Isomaltose | 72 | 76 | 11 |
| Sucrose plus Levanbiose | 288 | 4 | — |
| Sucrose plus Inulobiose | 276 | 8 | — |
| Sucrose plus Maltose | 78 | 74 | 9 |
| Sucrose plus Maltotriose | 213 | 29 | — |
| Sucrose plus Panose | 48 | 84 | 47 |
| Sucrose plus Isopanose | 282 | 4 | — |
| Sucrose plus Isomaltotriose | 36 | 88 | 49 |
| Sucrose plus 6-Kestose | 291 | 3 | — |
| Sucrose plus Maltotetraose | 255 | 15 | — |
| Sucrose plus Isomaltosyl maltose | 24 | 92 | 55 |
| Sucrose plus Isomaltotetraose | 18 | 94 | 58 |
| Sucrose plus Isomaltopentaose | 15 | 95 | 60 |
| Sucrose plus Maltopentaose | 264 | 12 | — |
| Sucrose plus Erythlitol | 290 | 3 | — |
| Sucrose plus Xylitol | 280 | 7 | — |
| Sucrose plus Sorbitol | 290 | 8 | — |
| Sucrose plus Mannitol | 286 | 5 | — |
| Sucrose plus Maltitol | 270 | 10 | — |
| Sucrose plus Isomaltitol | 270 | 10 | — |
| Sucrose plus Lactitol | 280 | 7 | — |
| Sucrose plus Maltotriitol | 262 | 13 | — |
| Sucrose plus Pannitol | 70 | 77 | — |
| Sucrose plus Isopannitol | 270 | 10 | — |
| Sucrose plus Isomaltotriitol | 60 | 80 | — |
| Sucrose plus Maltotetraitol | 236 | 21 | — |
| Sucrose plus Isomaltosyl maltitol | 48 | 84 | — |
| Sucrose plus Isomaltotetraitol | 45 | 85 | — |
| Sucrose plus Maltopentaitol | 265 | 12 | — |
| Sucrose plus Isomaltopentaitol | 66 | 78 | — |

As obvious from the experimental results as shown in the Columns, 70% or higher inhibition of water-insoluble glucan formation was noted with the use of isomaltosyl mono-glucose, i.e., panose or isomaltotriose; isomaltosyl di-glucose, i.e., isomaltosyl maltose or isomaltotetraose; isomaltosyl tri-glucose, i.e., isomaltopentaose; or reduction products thereof; i.e., pannitol, isomaltogriitol, isomaltosyl maltitol, isomaltotetraitol or isomaltopentaitol. Remarkably, an inhibition of up to about 90% or higher was noted with the use of either isomaltosyl di- or tri-glucose. The use of either isomaltose or maltose resulted in a relatively high inhibition degree which was, however, inferior to those attained with the use of the isomaltosyl mono-, di-, or tri-glucose.

In order to detail the inhibition of water-insoluble glucan formation from sucrose, another experiment was carried out by reducing the amounts of each saccharide to levels of 10% against sucrose: A mixture, consisting of 1 ml of 4 w/v % aqueous sucrose solution, 1 ml of 0.4 w/v % aqueous solution of each saccharide as listed in TABLE I, 1.5 ml of 0.1M phosphate buffer containing 0.05 w/v % NaN$_3$, and 0.5 ml of the enzyme solution (0.02 units, was incubated at 37° C. for 16 hours, and the water-insoluble glucan formation in the reaction mixture was determined according to the enzyme assay method. The results are given in Column C of TABLE I, wherein the inhibition degrees of water-insoluble glucan formation (%) were also calculated using the hereinbefore presented equation.

As obvious from the experimental results shown in Column C of TABLE I, only an extremely low inhibition was attained with the use of either isomaltose or maltose, whereas an inhibition of up to about 45–60% was obtained with the use of the isomaltosyl mono-, di-, or tri-glucoses, i.e., panose, isomaltotriose, isomaltosyl maltose, isomaltotetraose or isomaltopentaose despite of their presence in amounts compared with the amount of sucrose, i.e., only 10% against sucrose. Remarkably, an inhibition degree of about 85–60% was obtained with the use of isomaltosyl di- or tri-glucose. These findings support the use of these saccharides as low- or anti-cariogenic sweeteners.

EXPERIMENT 4

Acid formation

Organic acid formation from some saccharides by Streptococcus mutans was tested: Streptococcus mutans 6715 strain was cultivaed similarly as in EXPERIMENT 1, and the cells, obtained by centrifuging the culture, were washed with 0.9 w/v % sodium chloride solution, followed by additional centrifugation. Two ml of a mixture solution, consisting of 0.2 ml of the cell suspension, prepared from about 100 ml of the culture, 1.5 ml of Stephan's buffer, and 0.3 ml aqueous solution of each saccharide as listed in TABLE II, was incubated at 37° C. for 30 minutes, followed by pH-measurement of the reaction mixture. The Stephan's buffer was prepared by the method as reported by R. M. Stephan et al., Journal of Dental Research, Vol.26, pp.15–41 (1947): One ml of Solution I, prepared by dissolving 17.89 g Na$_2$HPO$_4$. 12H$_2$O, 7.92 g KOH and 6.81 g KH$_2$PO$_4$ in water to give a final volume of 100 ml, was placed in a 100-ml volumetric flask, and mixed with about 90 ml of water. To the flask was added 1 ml of Solution II, prepared by dissolving 4.54 g KH$_2$PO$_4$, 0.32 g MgSO$_4$.7H$_2$O, 0.57 g CaSO$_4$.2H$_2$O and 10 ml of 3.5% hydrochloric acid solution in water to give a final volume of 100 ml. This mixture was diluted with additional water to obtain 100 ml of Stephan's buffer (pH 7.0).

The results are given in TABLE II, wherein the organic acid formation from the saccharides can be estimated by the pH-values.

TABLE II

| Saccharide | pH-Level |
|---|---|
| Sucrose | 4.0 |
| L-Arabinose | 7.0 |
| L-Sorbose | 7.0 |
| L-Rhamnose | 7.0 |
| D-Galactose | 7.0 |
| D-Mannose | 5.5 |
| D-Glucose | 4.0 |
| Methyl-α-D-glucose | 7.0 |
| 2-Deoxy glucose | 7.0 |

TABLE II-continued

| Saccharide | pH-Level |
| --- | --- |
| Maltotetraose | 5.3 |
| Isomaltosyl maltose | 7.0 |
| Isomaltotetraose | 7.0 |
| Isomaltopentaose | 7.0 |
| Maltopentaose | 5.6 |
| Erythlitol | 7.0 |
| Xylitol | 7.0 |
| Sorbitol | 7.0 |
| Mannitol | 7.0 |
| Maltitol | 7.0 |
| Isomaltitol | 7.0 |
| Lactitol | 7.0 |
| Maltotriitol | 7.0 |
| Pannitol | 7.0 |
| Isopannitol | 7.0 |
| Isomaltotriitol | 7.0 |
| Maltotriitol | 7.0 |
| N—Acetyl glucosamine | 7.0 |
| Turanose | 7.0 |
| Lactulose | 7.0 |
| Gentibiose | 7.0 |
| Cellobiose | 7.0 |
| Melibiose | 7.0 |
| Trehalose | 7.0 |
| Maltulose | 7.0 |
| Isomaltose | 7.0 |
| Levanbiose | 6.5 |
| Inurobiose | 4.5 |
| Maltose | 4.0 |
| Maltotriose | 5.0 |
| Panose | 7.0 |
| Isopanose | 7.0 |
| Isomaltotriose | 7.0 |
| 6-Kestose | 6.8 |
| Isomaltosyl maltitol | 7.0 |
| Isomaltotetraitol | 7.0 |
| Maltopentaitol | 7.0 |
| Isomaltopentaitol | 7.0 |

The experimental results, as shown in TABLE II, confirm that no organic acid formation was noted with the present isomaltosyl mono-, di-, or tri-glucose, i.e., panose, isomaltotriose, isomaltosyl maltose, isomaltotetraose or isomaltopentaose, or reduction products thereof, i.e., pannitol, isomaltotriitol, isomaltosyl maltitol, isomaltotetraitol, or isomaltopentaitol.

From the hereinbefore described experimental results, it can be concluded that the present isomaltosyl mono-, di-, tri-glucoses and reduction products thereof are not significantly fermentable by oral cariogenic microorganisms into either organic acid or water-insoluble glucan and that acid formation from sucrose is strongly inhibited therewith.

The hereinafter disclosed embodiments are only illustrative and are not intended in any way to limit the scope of the invention.

EXAMPLE 1

Sweetener

Pullulan was dissolved in 0.66N hydrochloric acid solution to give a concentration of 10 w/v %, and the resultant solution was then incubated at 95° C. for 30 minutes. Thereafter, the mixture solution was cooled to 40° C., and sodium hydroxide added to give a pH level of 4.5.

While maintaining the temperature, the mixture was admixed with a glucoamylase (EC 3.2.1.3), purchased from Seikagaku-Kogyo Co. Ltd., Tokyo, Japan, in an amount of 29 units per g solid pulluan and then subjected to enzymolysis for 4 hours, followed by 15-minute incubation of the reaction mixture at 95° C. to suspend the enzymolysis.

The reaction mixture was decolourized with the use of activated carbon, deionized with the use of ion exchange resins of H- and OH-forms, and concentrated in vacuo to give a concentration of 30 w/w %.

"Dowex 50WX4" ($Mg^{2+}$)", a commercially-available strongly-acidic cation exchange resin of alkaline earth metal-form, a product of Dow Chemical Company, Midland, Mischigan, U.S.A., in an aqueous suspension, was packed in a jacketted stainless steel column, inside diameter of 6.2 cm, to give a bed depth of 10 m.

While keeping the temperature in the column at 60° C., the concentrate was added thereto in an amount of 3 v/v % against the bed volume, and then fractionated by charging thereto 60° C. hot water at a flow rate of SV 0.2, followed by harvest of the fractions with panose contents of 80% or higher.

The fractions were then decolored, deionized, concentrated, dried in vacuo, and pulverized in usual way to obtain a powder product with a moisture content of below 3% in a yield of about 5% against the starting pullulan solid.

The sugar composition of the powder product was as follows: maltose, 0.6%; isomaltose, 2.5%; panose, 85.5%; isomaltosyl maltose, 9.7%; and pantaose and higher oligosaccharides, 1.7%.

The desirable sweetness of the product renders it useful as a low-cariogenic sweetener.

EXAMPLE 2

Sweetener

A 5% aqueous pullulan solution at 45° C. and pH 5.0 was mixed with a β-amylase, purchased from Seikaga-ku-Kogyo Co. Ltd., Tokyo, Japan, and pullulanase (EC 3.2.1.41), a product of Hayashibara Biochemical Laboratories, Inc., Okayama, Japan, in respective amounts of 1,000 units per g pullulan solid and 100 units per g pullulan solid, and subjected to enzymolysis for 48 hours, followed by 15-minute incubation of the reaction mixture at 95° C. to suspend the enzymolysis. Then, the reaction mixture was purified, and concentrated similarly as in EXAMPLE 1.

"XT-1022E ($Na^+$)", a commercially-available stronglyacidic cation exchange resin of alkali metal-form, a product of Tokyo Chemical Industries, Kita-ku, Tokyo, Japan, in an aqueous suspension, was packed in four jacketted stainless steel columns, inside diameter of 5.4 cm, to give respective bed depths of 5 m and the columns cascaded to give a total bed depth of 20 m.

While keeping the temperature in the columns at 75° C., the concentrate was applied thereto in an amount of 10 v/v % against the bed volume, and then fractionated by charging therethrough 75° C. hot water at a flow rate of SV 0.13, followed by harvest of the fractions with isomaltosyl maltose contents of 70% or higher.

Similary as in EXAMPLE 1, the fractions were purified, concentrated, dried in vacuo, and pulverized to obtain a powder product with a moisture content of below 3% in the yield of about 52% against the starting pullulan solid.

The sugar composition of the powder product was as follows: disaccharides, 8.2%; panose, 11.8%; isomaltosyl maltose, 75.6%; and pentaose and higher oligosaccharides, 4.4%.

The relatively low sweetening power of the product renders it useful as a low-cariogenic sweetener and an additive to impart food products with appropriate viscosity and/or moisture.

EXAMPLE 3

Sweetener

To a 70 w/w % aqueous glucose solution was added an immobilized glucoamylase, prepared by the method as disclosed in Japan Kokai No. 124,494/80, and the mixture was incubated at 50° C. and pH 4.8 to a reversible-reaction product of glucose with an isomaltotriose content of 10.2%.

While maintaining the temperature in a column packed with a fresh preparation of the same resin as used in EXAMPLE 2 at 75° C., 45 w/w % solution of the reversible-reaction product was applied thereto in an amount of 5 v/v % against the bed volume, and then fractionated by charging therethrough 75° C. hot water at a flow rate of SV 0.2, followed by harvest of the fractions with isomaltotriose contents of 30% or higher.

Similarly as in EXAMPLE 1, the fractions were purified, concentrated, dried in vacuo, and pulverized to obtain a powder product with a moisture content of below 3% in a yield of about 40% against the starting pullulan solid.

The sugar composition of the powder product was as follows: glucose, 4.2%; isomaltose, 32.6%; isomaltotriose, 34.5%; isomaltotetraose, 19.6%; and higher oligosaccharides including isomaltopentaose, 9.1%.

The desirable sweetness of the product renders it useful as a low-cariogenic sweetener.

EXAMPLE 4

Sweetener

A 20 w/w % aqueous dextran solution, prepared by dissolving dextran in 1N sulfuric acid, was incubated at 100° C. for 60 minutes, and neutralized with 6N sodium hydroxide. Then, to give a concentration of 75 v/v %, and the upper-layer was harvested therefrom, followed by the removal of methanol. The resultant solution was deionized with the use of ion exchange resins of H- and OH-forms and concentrated in vacuo to give a concentration of 60 w/w %.

The resin used in EXAMPLE 2 was converted into K+-form in usual way and packed in a jacketted stainless steel column, inside diameter of 6.2 cm, to give a bed depth of 10 m.

While keeping the temperature in the column at 60° C., the concentrate was applied thereto in an amount of 3 v/v % against the bed volume, and then fractionated by charging therethrough 60° c. hot water at a flow rate of SV 0.3, followed by harvest of the fractions with isomaltotetraose contents of 30 w/w % or higher.

Similarly as in EXAMPLE 1, the fractions were purified, concentrated, dried in vacuo, and pulverized to obtain a powder product with a moisture content of below 3% in a yield of about 60% against the starting dextran solid.

The sugar composition of the powder product was as follows: isomaltose, 9.2%; isomaltotriose, 25.3%; isomaltotetraose, 37.3%; isomaltopentaose, 21.6%; and higher oligosaccharides including hexaose, 6.6%.

The desirable sweetness of the product renders it useful as a low-cariogenic sweetener.

EXAMPLE 5

Sweetener

A sweetener mixture, prepared by admixing 1 kg of a hydrogenated maltose syrup (moisture content 25%), and 250 g of a sweetener, obtained similarly as in EXAMPLE 1, had a sweetening powder comparable to that of sucrose. Thus the mixture can be advantageously used as a diet sweetener for those whose calorie intakes are restricted, e.g., diabetics or obese people, and as a low-cariogenic sweetener.

The sweetener mixture is resistant to the browning reaction upon heating. Hence it can be advantageously used for cooking various boiled- or baked food products with less fear of causing undesirable colorization, as well as for imparting an appropriate moisture, or gloss thereto.

EXAMPLE 6

Sweetener

A powder, obtained by admixing 900 g sucrose, 300 g of a commercially-available α-glycosyl stevioside, α-G-Sweet®, a product of Toyo Sugar Refining Co. Ltd., Tokyo, Japan, and 5 g of a sweetener, obtained similarly as in EXAMPLE 3, and pulverizing the resultant mixture, was sprayed with a small amount of water, and a relatively high pressure applied thereto to obtain a solid sweetener in cubic form.

The product is an ideal low-cariogenic sweetener with excellent taste and sweetness comparable to sucrose.

Addition of water readily dissolves the product, and a chilled solution thereof can be used as a soft drink without further processing.

EXAMPLE 7

Hard candy

Three kg of a sweetener, obtained similarly as in EXAMPLE 2, was dissolved in ten liters of a heated 55% aqueous sucrose solution, and the mixture was concentrated in vacuo to give a moisture content of below 2%. Thereafter, to the concentrate was admixed 100 g of citric acid, and small amounts of lemon flavor and coloring agent, and the mixture was shaped in the usual way to obtain the titled product.

The product is an ideal low-cariogenic hard candy. Six-month standing of the product did not cause any crystallization of its sucrose-constituent.

EXAMPLE 8

Chewing gum

After softening 2 kg gum base by heating, 2 kg of maltose powder, 3 kg of sucrose powder, 2 kg of a powder sweetener, obtained similarly as in EXAMPLE 4, and small amounts of menthol and coloring agent were added to the gum base, and the mixture was sufficiently kneaded in the usual way with the use of a roller, followed by shaping to obtain the titled product.

The product is an ideal low-cariogenic chewing gum with excellent chewing properties.

EXAMPLE 9

Chocolate

A composition, consisting of 40 kg of cacao paste, 10 kg of cacao butter, 5 kg of a powder sweetener, obtained similarly as in EXAMPLE 1, 7 kg of sucrose, 3 kg of crystalline maltitol and 20 kg of whole milk, was sufficiently kneaded, and the resultant mixture was placed in a refiner to reduce its particle size. The content of the refiner was then transferred into a conche, and with 500 g of lecithin added, followed by 2-day kneading at 50° C. Thereafter, the content was placed in a shaping machine, solidified, and shaped in usual way to obtain the titled product.

The product is an ideal low-cariogenic chocolate with mild taste and flavour, and, during storage, neither sugar- nor fat-blooming occur.

EXAMPLE 10

Sour milk beverage

After pasteurizing at 80° C. for 20 minutes, 10 kg of defatted milk was cooled to 40° C., and admixed with 300 g of a starter, followed by 10 hour incubation of the resultant at 35°–37° C. Thereafter, the culture product was homogenized, and admixed with 4 kg of a powder sweetener, obtained similarly as in EXAMPLE 3, 1 kg of sucrose and 2 kg of isomerized sugar syrup, followed by additional incubation at 70° C. to effect pasteurization. After cooling to the ambient temperature, the mixture was admixed with a small amount of flavor, and finally bottled to obtain the titled product.

The product is a sour milk beverage with harmonized flavor and sour sweetness.

EXAMPLE 11

Strawberry jam

Fifteen kg of raw strawberry, 6 kg of sucrose, 2 kg of maltose, 4 kg of a sweetener, obtained similarly as in EXAMPLE 2, 50 g of pectin, and 10 g citric acid were boiled up together in a pot to obtain the titled product, followed by bottling of the product.

The product is an ideal low-cariogenic strawberry jam with excellent flavor and gloss.

EXAMPLE 12

"Tsukudani"

Two hundred and fifty kg of raw tangle was treated to remove the sand stuck thereto, soaked in an acid solution, and cut into squares, in usual way. Then, the tangle was soaked in a mixture consisting of 212 ml soy sauce, 318 ml of amino acid solution, 70 g of a sweetener, obtained similarly as in EXAMPLE 4, and 20 g of sucrose. While boiling the mixture, 10 g of sodium glutamate, and 8 g of caramel were added thereto. The mixture was finally boiled up to obtain the titled product "TSUKUDANI"—a typical Japanese-style preserved food.

The product is an appetizing low-cariogenic "TSUKUDANI" with excellent taste, flavor, color and gloss.

EXAMPLE 13

Tablet

A composition, consisting of 50 g of acetyl-salicylic acid, 4 g of corn starch, and 14 g of a powder sweetener, obtained similarly as in EXAMPLE 1, was sufficiently kneaded, and the resultant mixture was tabletted with the use of a tabletting machine equipped with 20 R-punch of 12 mm diameter to obtain low-cariogenic tablets, 680 mg each, 5.25 mm thick with a hardness of 8±1 kg.

The tablet can be easily administered due to its sweetness, and, over long periods of storage, neither cracking nor deformation occur.

EXAMPLE 14

Tooth paste

A composition with a formulation of $CaHPO_4$, 45.0%; pullulan, 2.95%; sodium lauryl sulfate, 1.5%; glycerin, 20.0%; polyoxyethylene sorbitan ester, 0.5%; antiseptic agent, 0.05%; a sweetener, obtained similarly as in EXAMPLE 4, 12.0%; sucrose, 5.0%; and water, 13.0%, was sufficiently kneaded in usual way to obtain the titled product.

The appropriate sweetness of the product renders it useful as a tooth paste for children.

EXAMPLE 15

Sweetener

An 50% aqueous solution of a powder product containing panose as the predominant constituent, obtained similarly as in EXAMPLE 1, was placed in an autoclave, and admixed with 10% Raney nickel catalyst. Then, the mixture was heated to 90°–120° C. while stirring, and hydrogenated therein at this temperature under a hydrogen pressure of 20–120 $kg/cm^2$, followed by removal of the catalyst. Thereafter, the residue was decolourized with the use of activated carbon, and deionized with the use of ion exchange resins of H- and OH-forms, concentrated in vacuo, and pulverized to obtain a powder product with a moisture content of below 3% in the yield of about 4% against the starting pullulan solid.

The sugar composition of the powder product was as follows: sorbitol, 0.3%; maltitol, 0.8%; isomaltitol, 2.8%; pannitol, 84.9%; isomaltosyl maltitol, 9.6%; and reduction products of pentaose and higher oligosaccharides, 1.6%.

The desirable sweetness of the product renders it useful as a low-cariogenic sweetener.

EXAMPLE 16

Sweetener

The hydrogenation of the powder product containing isomaltosyl maltose as the predominant constituent, obtained similarly as in EXAMPLE 2, was carried out similarly as in EXAMPLE 15, and the resultant was purified, concentrated, dried in vacuo, and pulverized to obtain a powder product with a moisture content of below 3% in the yield of about 46% against the starting solid pullulan.

The sugar composition of the product was as follows: sorbitol, 0.2%; hydrogenated disaccharides, 8.3%; isomaltosyl maltitol, 75.4%; pannitol, 12.0%; and reduction products of pentaose and higher oligosaccharides, 4.1%.

The relatively low sweetness of the product renders it useful as a low-cariogenic sweetener, as well as an additive to impart appropriate viscosity and moisture to food products.

EXAMPLE 17

Sweetener

The hydrogenation of a powder product containing isomaltotriose and isomaltotetraose as the predominant constituents, obtained similarly as in EXAMPLE 3, was carried out similarly as in EXAMPLE 15, and the reaction mixture was purified, concentrated, dried in vacuo, and pulverized to obtain a powder product with a moisture content of below 3% in the yield of about 35% against the starting solid glucose.

The sugar composition of the product was as follows: sorbitol, 4.6%; isomaltitol, 32.5%; isomaltotriitol, 34.6%; isomaltotetraitol, 19.4%; and reduction products of pentaose and higher oligosaccharides including isomaltopentaitol, 8.9%.

The desirable sweetness of the product renders it useful as a low-cariogenic sweetener.

EXAMPLE 18

Sweetener

A powder product containing isomaltotriose, isomaltotetraose and isomaltopentaose as the predominant constituents, obtained similarly as in EXAMPLE 4, was hydrogenated similarly as in EXAMPLE 15, and the resultant was purified, concentrated, dried in vacuo, and pulverized to obtain a powder product with a moisture content of below 3% in the yield of about 52% against the starting solid dextran.

The sugar composition of the product was as follows: sorbitol, 0.3%; isomaltitol, 9.4%; isomaltotriitol, 25.3%; isomaltotetraitol, 37.4%; isomaltopentaitol, 21.3%; and reduction products of hexaose and higher oligosaccharides, 6.3%.

The desirable sweetness of the product renders it useful as a low-cariogenic sweetener.

EXAMPLE 19

Sweetener

A sweetener mixture, prepared by dissolving 250 g of a sweetener, obtained similarly as in EXAMPLE 15, in 1 kg of hydrogenated maltose syrup (moisture content 25%), had a sweetening power comparable to that of sucrose. Thus, the sweetener can be advantageously used as a dietary sweetener for those whose calorie-intakes are restricted, e.g., diabetics or obese people, as well as a low-cariogenic sweetener.

The sweetener mixture is resistant to the browning reaction upon heating. Hence, the sweetener can be advantageously used for cooking various boiled or baked food products with less fear of causing colorization, in addition to the use for imparting thereto an appropriate viscosity, moisture or gloss.

EXAMPLE 20

Sweetener

A powder product, obtained by admixing 900 g sucrose, 600 g of crystalline maltitol, 100 g of a sweetener, obtained similarly as in EXAMPLE 17, and 5 of a commercially-available α-glycosyl stevioside, α-G-Sweet®, a product of Toyo Sugar Refining Co. Ltd., Tokyo, Japan, and pulverizing the resultant mixture, was sprayed with a small amount of water, and a relatively high pressure applied thereto to obtaining a solid sweetener in cubic form.

The product is an ideal low-cariogenic sweetener with excellent taste and sweetness comparable to sucrose.

Addition of water readily dissolves the product, and a chilled solution thereof can be used as a soft drink without further processing.

EXAMPLE 21

Hard candy 3 kg of a sweetener, obtained similarly as in EXAMPLE 16, was dissolved in 10 liters of a heated 55% aqueous sucrose solution, and the mixture was concentrated in vacuo to give a moisture content of below 2%. Thereafter, to the concentrate was added 100 g citric acid and small amounts of lemon flavor and coloring agent, and the mixture was shaped in usual way to obtain the titled product.

The product is an ideal low-cariogenic hard candy. Six-month standing of the product did not cause any crystallization of the sucrose constituent.

EXAMPLE 22

Chewing gum

After softening 2 kg of gum base by heating, to the gum base was added 2 kg of maltose powder, 4 kg of a powder sweetener, obtained similarly as in EXAMPLE 18, and small amounts of menthol and coloring agent. The mixture was sufficiently kneaded in usual way with the use of a roller, followed by shaping it into the titled product.

The product is an ideal low-cariogenic chewing gum with excellent chewing properties.

EXAMPLE 23

Chocolate

A composition, consisting of 40 kg of cacao paste, 10 kg of cacao butter, 2 kg of a powder sweetener, obtained similarly as in EXAMPLE 15, 7 kg of sucrose, 6 kg of crystalline maltitol, and 20 kg of whole milk, was sufficiently kneaded, and the resultant mixture was placed in a refiner to reduce its particle size. The content of the refiner was then transferred into a conche, and admixed with 500 g of lecithin, followed by 2-day kneading at 50° C. Thereafter, the content was placed in a shaping machine, solidified, and shaped in usual way to obtain the titled product.

The product is an ideal low-cariogenic chocolate with a mild taste, and, during storage, neither sugar- nor fat-blooming occur.

EXAMPLE 24

Sour milk beverage

After pasteurizing at 80° C. for 20 minutes, 10 kg of defatted milk was cooled to 40° C., and admixed with 300 g of a starter, followed by 10-hour incubation of the resultant product at 35°–37° C. Thereafter, the cultured product was homogenized, and admixed with 4 kg of a powder sweetener, obtained similarly as in EXAMPLE 17, 1 kg of sucrose and 2 kg of isomerized sugar syrup, followed by additional incubation at 70° C. to effect pasteurization. After cooling the resultant to the ambient temperature, the mixture was admixed with a small amount of flavor, followed by bottling to obtain the titled product.

The product is a sour milk beverage with harmonized flavor and sour sweetness.

EXAMPLE 25

Strawberry jam

Fifteen kg of raw strawberry, 6 kg of sucrose, 2 kg of maltose, 4 kg of a sweetener, obtained similarly as in EXAMPLE 16, 50 g of pectin, and 10 g of citric acid were boiled up together in a pot to obtain the titled product, followed by bottling of the jam product.

The product is an ideal low-cariogenic strawberry jam with excellent flavor and gloss.

EXAMPLE 26

"Tsukudani"

Two hundred and fifty g of raw tangle was treated to remove the sand stuck thereto, soaked in acid solution, and cut into squares, in usual way. Then, the tangle was soaked in a mixture consisting of 212 ml of soy sauce, 318 ml of amino acid solution, 70 g of a sweetener, obtained similarly as in EXAMPLE 18, and 2 g of sucrose. While boiling the mixture, 12 g of sodium glutamate, and 8 g of caramel were admixed thereto. The mixture was finally boiled up to obtain the titled product, "TSUKUDANI"—a typical Japanese-style preserved food.

The product is an appetizing low-cariogenic "TSUKUDANI" with excellent taste, flavor, color and gloss.

EXAMPLE 27

Tablet

A composition, consisting of 50 g of acetyl-salicylic acid, 4 g of corn starch, 6 g of sucrose, 4 g of maltose, and 4 g of a sweetener, obtained similarly as in EXAMPLE 15, was sufficiently kneaded, and the resultant mixture was tabletted with the use of a tabletting machine equipped with 20 R-punch of 10 mm diameter to obtain low-cariogenic tablets, 680 mg each, 5.25 mm thick, and with a hardness of $8 \pm 1$ kg.

The product can be easily administrated due to its appropriate sweetness and over long periods of storage neither cracking nor deformation occur.

EXAMPLE 28

Tooth paste

A composition with a formulation of $CaHPO_4$, 45.0%; pullulan, 2.95%; sodium laulyl sulfate, 1.5%; glycerin, 20.0%; polyoxyethylene sorbitan ester, 0.5%; antiseptic agent, 0.05%; a sweetener, obtained similarly as in EXAMPLE 18, 12.0%; sucrose, 5.0%; and water, 13.0%, was sufficiently kneaded in usual way to obtain the titled product.

The appropriate sweetness of the product renders it useful as a tooth paste for children.

We claim:

1. In an orally-usable product containing sucrose as a sweetener, the improvement whereby a low- or anti-cariogenic property is imparted to the product, wherein said product comprises a substance selected from the group consisting of isomaltosyl mono-, di-, tri-glucoses, reduction products thereof and mixtures thereof, said substance being present in an amount effective to impart a low- or anti-cariogenic property to the product, said amount being at least 5% on the dry solid basis.

2. A product as set forth in claim 1, which is in the form of a liquid.

3. A product as set forth in claim 1, which is in the form of a paste.

4. A product as set forth in claim 1, which is in the form of a solid.

5. A product as set forth in claim 1, which is a food or drink for human consumption.

6. A product as set forth in claim 1, which is a member selected from the group consisting of feed, pet food, cosmetic, dentifrice and tobacco.

7. A product as set forth in claim 1, which is a sweetener.

8. A product as set forth in claim 1, wherein said substance is an isomaltosyl mono-glucose selected from the group consisting of panose, isomaltotriose and mixtures thereof.

9. A product as set forth in claim 1, wherein said substance is an isomaltosyl di-glucose selected from the group consisting of isomaltosyl maltose, isomaltotetraose and mixtures thereof.

10. A product as set forth in claim 1, wherein said substance is the isomaltosyl tri-glucose isomaltopentaose.

11. A product as set forth in claim 1, wherein said substance is a reduction product of isomaltosyl mono-glucose selected from the group consisting of pannitol, isomaltotriitol and mixtures thereof.

12. A product as set forth in claim 1, wherein said substance is a reduction product of isomaltosyl di-glucose selected from the group consisting of isomaltosyl maltitol, isomaltotetraitol and mixtures thereof.

13. A product as set forth in claim 1, wherein said substance is the reduction product of isomaltosyl tri-glucose, isomaltopentaitol.

14. A method for imparting a low- or anti-cariogenic property to an orally-usable product containing sucrose as a sweetener, comprising incorporating into said product, a substance selected from the group consisting of isomaltosyl mono-, di-, or tri-glucose, reduction products thereof and mixtures thereof, in an amount, effective to impart such property to the product, of at least 5% on the dry solid basis.

15. A method as set forth in claim 14, wherein said product is in the form of a liquid.

16. A method as set forth in claim 14, wherein said product is in the form of a paste.

17. A method as set forth in claim 14, wherein said product is in the form of a solid.

18. A method as set forth in claim 14, wherein said product is a food or drink for human consumption.

19. A method as set forth in claim 14, wherein said product is a member selected from the group consisting of feed, pet food, cosmetic, dentifrice and tobacco.

20. A method as set forth in claim 14, wherein said substance is an isomaltosyl mono-glucose selected from the group consisting of panose, isomaltotriose and mixtures thereof.

21. A method as set forth in claim 14, wherein said substance is an isomaltosyl di-glucose selected from the group consisting of isomaltosyl maltose, isomaltotetraose and mixtures thereof.

22. A method as set forth in claim 14, wherein said substance is the isomaltosyl tri-glucose isomaltopentaose.

23. A method as set forth in claim 14, wherein said substance is a reduction product of isomaltosyl mono-glucose selected from the group consisting of pannitol, isomaltotriitol and mixtures thereof.

24. A method as set forth in claim 14, wherein said said substance is the reduction product of isomaltosyl di-glucose selected from the group consisting of isomaltosyl maltitol, isomaltotetraitol and mixtures thereof.

25. A method as set forth in claim 14, wherein said substance is the reduction product of isomaltosyl tri-glucose, isomaltopentaitol.

* * * * *